Figure 1:
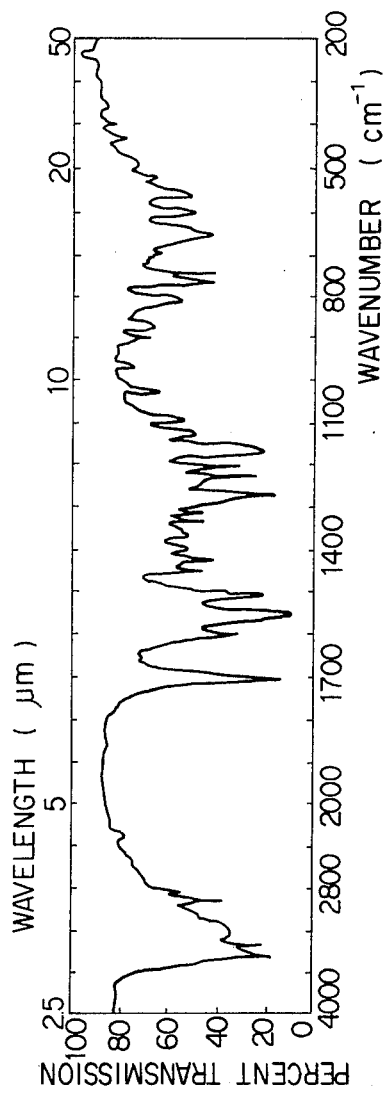

United States Patent [19]

Takita et al.

[11] 4,409,240
[45] Oct. 11, 1983

[54] DERIVATIVES OF DIHYDROXYBENZOIC ACID AND PHARMACEUTICAL COMPOSITION THEREOF

[75] Inventors: Hitoshi Takita; Yutaka Mukaida; Sakuo Noda; Hidetoshi Kobayashi, all of Tokyo, Japan

[73] Assignee: Kureha Kagaku Kogyo Kabushiki Kaisha, Tokyo, Japan

[21] Appl. No.: 349,372

[22] Filed: Feb. 16, 1982

[30] Foreign Application Priority Data

Feb. 24, 1981 [JP] Japan .................. 56-25991

[51] Int. Cl.³ ................. A61K 31/195; C07C 101/30
[52] U.S. Cl. ..................................... 424/319; 424/309; 562/444; 562/451; 560/42; 560/39
[58] Field of Search .................. 562/444, 451; 560/42, 560/39; 424/319, 309

[56] References Cited

U.S. PATENT DOCUMENTS

| | | | |
|---|---|---|---|
| 3,769,334 | 10/1973 | Garzia | 562/444 |
| 3,769,335 | 10/1973 | Garzia | 562/444 |
| 3,781,328 | 12/1973 | Witte et al. | 562/451 |
| 3,927,082 | 12/1975 | Katori et al. | 562/444 |
| 4,121,815 | 9/1980 | Weyer et al. | 562/451 |
| 4,182,775 | 1/1980 | Weyer et al. | 562/451 |
| 4,243,678 | 1/1981 | Krastinat | 562/444 |

OTHER PUBLICATIONS

Chemical Abstracts, vol. 85, No. 19, 1976, 85:142860j.
Chemical Abstracts, vol. 85, Dec. 6, 1976, No. 23, 85:177027v.

Primary Examiner—James H. Reamer
Attorney, Agent, or Firm—Wegner & Bretschneider

[57] ABSTRACT

A novel derivative of dihydroxybenzoic acid represented by the formula (I)

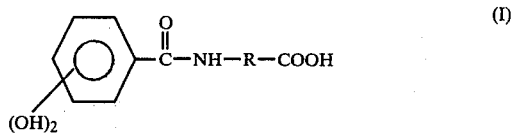

wherein R represents

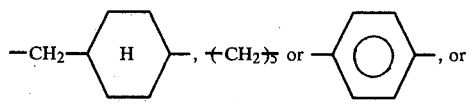

or a salt or an ester thereof which has specific pharmacological activities, a method for preparing thereof and a pharmaceutical composition comprising thereof as an active ingredient are provided.

5 Claims, 3 Drawing Figures

DERIVATIVES OF DIHYDROXYBENZOIC ACID AND PHARMACEUTICAL COMPOSITION THEREOF

The present invention relates to novel compounds, a method for preparing thereof and a pharmaceutical composition comprising thereof. More particularly, the present invention relates to novel derivatives of dihydroxybenzoic acid which have specific pharmacological activities.

It is an object of the present invention to provide novel derivatives of dihydroxybenzoic acid or salts or esters thereof. Another object of the present invention is to provide a method for preparing the novel derivatives. Furthermore, still another object of the present invention is to provide a pharmaceutical composition comprising a pharmaceutically effective amount of the novel derivative as an active ingredient.

The novel compounds according to the present invention are derivatives of dihydroxybenzoic acid (hereinafter referred to as the present compounds) represented by the formula (I):

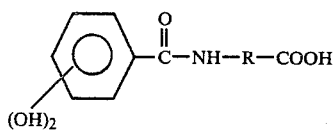

(I)

wherein R represents

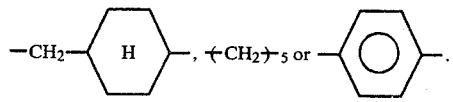

In the general formula (I), the cyclohexane ring includes both trans- and cis form.

The present compounds represented by the formula (I) include the following compounds:
4-[N-(2',3'-dihydroxybenzoyl)aminomethyl]cyclohexane-1-carboxylic acid,
4-[N-(2',4'-dihydroxybenzoyl)aminomethyl]cyclohexane-1-carboxylic acid,
4-[N-(2',5'-dihydroxybenzoyl)aminomethyl]cyclohexane-1-carboxylic acid,
4-[N-(2',6'-dihydroxybenzoyl)aminomethyl]cyclohexane-1-carboxylic acid,
4-[N-(3',4'-dihydroxybenzoyl)aminomethyl]cyclohexane-1-carboxylic acid,
4-[N-(3',5'-dihydroxybenzoyl)aminomethyl]cyclohexane-1-carboxylic acid,
4-[N-(2',3'-dihydroxybenzoyl)amino]benzoic acid,
4-[N-(2',4'-dihydroxybenzoyl)amino]benzoic acid,
4-[N-(2',5'-dihydroxybenzoyl)amino]benzoic acid,
4-[N-(2',6'-dihydroxybenzoyl)amino]benzoic acid,
4-[N-(3',4'dihydroxybenzoyl)amino]benzoic acid,
4-[N-(3',5'-dihydroxybenzoyl)amino]benzoic acid,
6-[N-(2',3'-dihydroxybenzoyl)amino]caproic acid,
6-[N-(2',4'-dihydroxybenzoyl)amino]caproic acid,
6-[N-(2',5'-dihydroxybenzoyl)amino]caproic acid,
6-[N-(2',6'-dihydroxybenzoyl)amino]caproic acid,
6-[N-(3',4'-dihydroxybenzoyl)amino]caproic acid,
6-[N-(3',5'-dihydroxybenzoyl)amino]caproic acid.

The present compounds include salts or esters of the derivative of dihydroxybenzoic acid. The salt is an alkali or alkaline earth metal salt such as sodium salt, potassium salt, calcium salt, magnesium salt, etc., or substituted- or non-substituted ammonium salt. The ester is a lower alkyl ester of which the alkyl group has 1 to 3 carbon atoms, such as a methyl-, ethyl-, or n- or isopropyl group.

The present compounds have excellent pharmacological activities such as inhibitory effects on platelet aggregation and polynuclear leukocyte migration and are pharmacologically safe. Accordingly, the present compounds are important compounds for use as a pharmaceutical in treating various diseases such as inflammation, thrombosis and the like, and an industrially important compound as an intermediate of medicaments.

The present compounds are preferably prepared according to the following reaction formula, although it may be prepared by the conventional method.

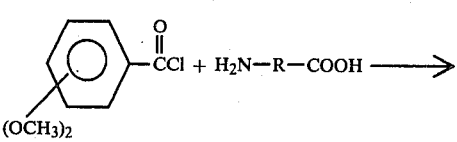

(veratroyl chloride)

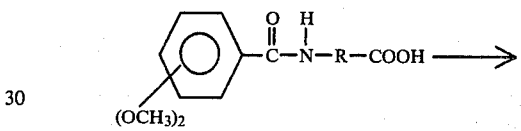

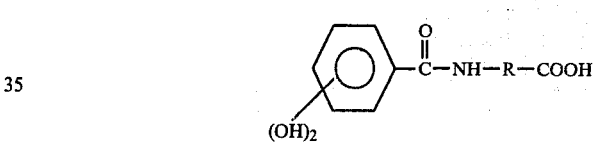

wherein R represents the same meaning as above. The first reaction, called Schotten-Bauman reaction, is carried out in a solvent such as a mixed solvent of polar solvent (e.g. dioxane) and water in the presence of 2 to 3 equivalents of sodium hydroxide based on veratroyl chloride at a temperature of 5° to 30° C. The second reaction is carried out in the presence of a de-methylation agent. The reaction temperature thereof is 80° to 130° C. when anhydrous aluminum trihalide such as AlCl$_3$ or AlBr$_3$ is used as the above-mentioned agent in a molar amount of 5 to 10, and it is $-78°$ to 12° C. when anhydrous boron trihalide is used in a molar amount of more than 2.

Another method for preparing the present compounds is as follows: A dihydroxybenzoic acid chloride represented by the formula (II):

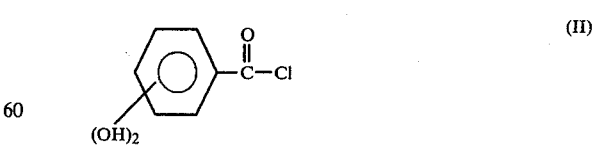

(II)

is brought into reaction with a hydrochloric acid salt of an aminocarboxylic acid derivative represented by the formula (III):

NH$_2$—R—COOH.HCl    (III)

wherein R represents the same meaning as above or a lower alkyl ester thereof, to obtain the present compound (acid- or ester form). The reaction is carried out in the presence of a de-hydrochlorination agent such as trialkylamine of which an alkyl group has 1 to 4 carbon atoms in a molar amount of more than 2 at a temperature of 5° to 30° C.

The salt form of the present compound is prepared by the conventional method for neutralization by using a base such as hydroxide, carbonate or bicarbonate of an alkali or an alkaline earth metal for example sodium, potassium, calcium or magnesium, ammonium or primary-, secondary- or tertiary amine.

The method mentioned above is only an embodiment of the method for preparing the present compound, and the method of the present invention is not restricted to the method as above.

The present compound shows an inhibitory effect on platelet aggregation and/or polynuclear leukocyte migration and a low acute toxicity, as is shown in Examples. Accordingly, the present compound is a useful substance as itself or an active ingredient of pharmaceutical composition for treating several diseases such as inflammation, thrombosis, cerebral hemorrhage, hypertension, asthma, and the like, and further as an intermediate of the medicaments.

When the present compound is used for a pharmaceutics, the salt or the ester must be pharmaceutically acceptable.

Furthermore, the present compound may be used as an active ingredient of a pharmaceutical composition for the above-mentioned diseases.

The present compound can be administered perorally, rectally or through injection in the various dosage forms as a composition together with a pharmaceutically acceptable carrier and/or an adjuvant. In these cases, a mixture of two or more kinds of the present compound or a mixture together with other pharmaceutically active materials may be used as an active ingredient of a pharmaceutical composition.

The dosage form of the composition may be tablet, sublingual tablet, powder, capsule, troache, aqueous or oily solution, suspension, emulsion, syrup, aqueous or oily injection. An example of the carrier mentioned above is water, gelatin, lactose, starch, pectin, magnesium stearate, stearic acid, talc, vegetable oil, gum arabic, polyalkylene glycol, vaseline, sorbitan trioleate, polyoxyethylene-sorbitan monooleate, alkylphenol, aliphatic alcohol, polyvinylpyrrolidone or the like. In the composition, if necessary, edulcorant, flavor, tinctorial agent, preservative, salt for osmoregulation or buffer, that is, the conventional pharmaceutical adjuvant may be used together.

The content of the present compound in the pharmaceutical composition may be adequately varied, however, it is 0.01%–100% by weight, preferably 0.05%–80% by weight of the composition.

The pharmaceutical composition of the present invention is administered to a human or animal parenterally, for example, rectally, through injection (hypodermic, intramuscular or intravenous, or drip), preferably perorally (for example sublingual etc.).

A dose of the pharmaceutical composition of the present invention is 0.1 to 500 mg, preferably 0.5 to 200 mg per day per one kilogram of the body weight in the case of peroral administration of a human, and 0.01 to 200 mg, preferably 0.1 to 100 mg in the case of parenteral administration, and the pharmaceutics is administered one to four times a day. However the dose of pharmaceutical composition depends on age, individuality, condition of a disease etc. of a human or animal, and the dose out of the above-mentioned range may be used.

The following is a more detailed explanation of the present invention; while referring to examples, however, it should be understood that the scope of the present invention is never restricted to Examples shown as follows.

PREPARATION OF THE PRESENT COMPOUND

EXAMPLE 1

Preparation of trans-4-[N-(3',4'-dihydroxybenzoyl)aminomethyl]cyclohexane-1-carboxylic acid In a 100-ml flask, 10 g (58.1 m mol) of protocatechuic acid and 20 ml of dehydrated and purified ethylether were introduced, and while stirring 25 g (210 m mol) of thionyl chloride was dropped into the flask under atmospheric nitrogen. After stirring the mixture for 24 hours at room temperature to bring the mixture into reaction, ether and excess thionyl chloride were evaporated off to obtain a viscous liquid pale yellow in colour. After adding 50 ml of dehydrated ether to the mixture and then removing the thus separated colourless powder by filtration, the solvent was evaporated off from the filtrate to obtain 7.5 g of crude protocatechuic acid chloride as a viscous pale yellow liquid.

In the next place, into 200 ml three-necked flask, 7.5 g of the thus obtained protocatechuic acid chloride 12.6 g (65.4 m mol) of ethyl trans-4-aminomethylcyclohexane-1-carboxylate.HCl, 16 g of triethylamine and 60 ml of benzene were introduced, and after stirring the mixture for 2 hours at room temperature under atmospheric nitrogen to bring the mixture into reaction, the solvent was evaporated off to obtain 30 g of the evaporation residue. After adding 45 ml of distilled water to the residue and then making the residue acidic with the addition of 1 N hydrochloric acid, the residue was extracted with ethyl acetate.

By dehydrating the residue and removing the solvent from the extract, 10.35 g of crude product of the titled compound was obtained, which was hydrolyzed with 21 ml of 4 N sodium hydroxide solution and 60 ml of ethanol by heating under a reflux condensed. After removing the solvent from the hydrolyzation product, it was acidified with 1 N hydrochloric acid and extracted with ethyl acetate. By dehydrating and removing the solvent from the extract, 8 g of crude trans-4-[N-(3',4'-dihydroxybenzoyl)aminomethyl]cyclohexane-1-carboxylic acid was obtained. By purifying the crude product through silicagel-columnchromatography and recrystallisation, 3.1 g of purified product was obtained in the form of a colorless powder.

The characteristics of the present compound (acid form) thus obtained were as follows:

(1) melting point on a hot plate; 212° to 214° C.

| | (2) elementary analysis; | | |
|---|---|---|---|
| | C (%) | H (%) | N (%) |
| theoretical: | 61.42 | 6.60 | 4.80 |
| experimental: | 61.2 | 6.53 | 4.77 |

(3) nuclear magnetic resonance (NMR) spectrum in dimethyl sulfoxide; $\delta = 0.86–1.84$ (9H, m), 1.99–2.08

(1H), 3.06 (2H), 6.75 (1H,d), 7.21 (1H, d), 7.28 (1H, s), 8.10 (1H), 8.56–10.56 (3H).

(4) infrared absorption (IR) spectrum by KBr tablet method; Shown in FIG. 1.

EXAMPLE 2

Preparation of 6-[N-(3′,4′-dihydroxybenzoyl)-amino]caproic acid

In a 2-neck 100 ml-round bottom flask, 10.0 g (54.9 m mol) of veratric acid was dissolved in 50 ml of benzene, and after adding 2 to 3 drops of pyridine to the solution, 13 g (109 m mol) of thionyl chloride was dropped into the solution while stirring the solution at room temperature within 3 min. Then the content was heated to 70° to 80° C. on a water bath, and maintained at the temperature for 2 hours under a reflux condenser and agitation. Then, the solvent and excess thionyl chloride were evaporated off under a reduced pressure to obtain 11.0 g of veratroyl chloride as colourless powder in a yield of 100%.

In a 200 ml-beaker, 9.0 g (68.8 m mol) of 6-aminocaproic acid was dissolved in 55 ml of distilled water, and 17 ml of dioxan and 17 ml of 4 N sodium hydroxide solution were added to the solution.

While immersing the beaker in a water bath and stirring the solution in the beaker, 11.0 g of veratroyl chloride (obtained as above) and 17 ml of 4 N sodium hydroxide solution were added to the solution gradually while maintaining the temperature of the mixture not higher than 30° C. to obtain a transparent reaction mixture of pale yellow in colour. By pouring the reaction mixture into 9 ml of concentrated hydrochloric acid in a 200-ml beaker, colourless powdery crystals separated out in the beaker. After collecting the crystals by filtering, drying the collected crystals and recrystallizing from 275 ml of a mixed solvent of water and ethanol (mixing ratio; 10:2), 12.7 g of 6-[N-(3′,4′-dimethoxybenzoyl)amino]caproic acid was obtained as colourless acicular crystals melting at 137.0° to 138.0° C. in a yield of 78.4%. The elementarily analytical data on the thus prepared compound were as follows:

|  | C (%) | H (%) | N (%) |
|---|---|---|---|
| experimental: | 60.70 | 7.20 | 4.70 |
| theoretical: | 61.00 | 7.17 | 4.74 |

In the next step, 6.0 g (20.3 m mol) of the thus obtained 6-[N-(3′,4′-dimethoxybenzoyl)-amino]caproic acid and 100 g of boron trichloride were introduced into a 200 ml-pear-shaped flask and the mixture was left to react at −78° C. in a dry-ice/methanol bath for 3 days under moisture-less conditions. After bringing the reaction mixture to room temperature and evaporating boron trichloride off under a normal pressure, 30 ml of distilled water was added to the reaction mixture and the mixture was stirred at room temperature. After collecting the thus separated colourless powdery insoluble material by filtering the mixture and drying the powdery material, 40 ml of distilled water was added to the material, and the mixture was stirred for one hour at room temperature to dissolve the material into water. After removing the still water-insoluble fractions by filtering the aqueous solution, the filtrate was freeze-dried to obtain 1.716 g of 6-[N-(3′,4′-dihydroxybenzoyl)amino]caproic acid as colourless powdery in a yield of 31.6%.

The characteristics of the present compound thus obtained were as follows:

(1) melting point on a capillary; 113.0°–115.0° C.

| (2) elementary analysis; | | | |
|---|---|---|---|
|  | C (%) | H (%) | N (%) |
| theoretical: | 58.42 | 6.41 | 5.24 |
| experimental: | 58.30 | 6.55 | 5.40 |

Figure 2:
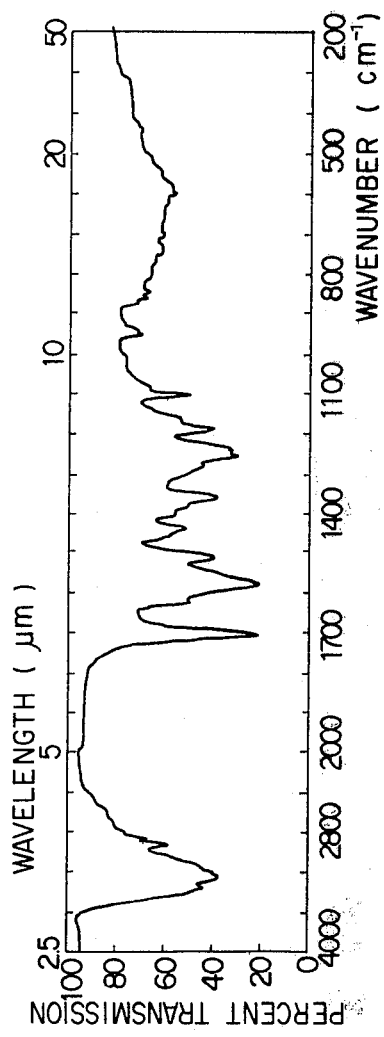

(3) infrared absorption (IR) spectrum by KBr tablet method; shown in FIG. 2.

EXAMPLE 3

Preparation of 4-[N-(3′,4′-dihydroxybenzoyl)amino]benzoic acid

Into a 200 ml-beaker, 55 ml of distilled water, 40 ml of dioxan and 9.40 g (68.5 m mol) of 4-aminobenzoic acid were introduced, and while stirring the mixture at room temperature, 17 ml of 4 N sodium hydroxide solution was added to the mixture to dissolve the solid raw material. Then, while stirring the solution in the beaker immersed in a water bath, 11.0 g of veratroyl chloride prepared by the same procedures as in Example 2 and 17 ml of 4 N sodium hydroxide solution were added to the solution gradually within 20 min. Then a reaction was carried out by maintaining the temperature of the mixture lower than 30° C. to obtain a reaction mixture of pale yellow in colour. By pouring the reaction mixture into 9 ml of concentrated hydrochloric acid in a 200 ml-beaker, colourless powdery crystals were obtained as a precipitate. After collecting the crystals by filtration and drying recrystallization was carried out by 650 ml of a mixed solvent of water and ethanol (mixing ratio; 1:1) on the powdery crystal to obtain 9.1 g of 4-[N-(3′,4′-dimethoxybenzoyl)amino]benzoic acid as colourless cotton-wool-like crystals melting at 247.0° to 248.5° C. in a yield of 55.0%. The elementarily analytical data were as follows:

|  | C (%) | H (%) | N (%) |
|---|---|---|---|
| experimental: | 63.50 | 5.10 | 4.50 |
| theoretical: | 63.78 | 5.02 | 4.65 |

In the next step, after introducing 25 g (187 m mol) of anhydrous aluminum chloride and 220 ml of freshly distilled nitrobenzene into a 500 ml-conical flask provided with a reflux condenser and a tube filled with anhydrous calcium chloride and dissolving anhydrous aluminum chloride by heating the content of the flask to 120° to 130° C., 6.0 g (19.9 m mol) of 4-[N-(3′,4′-dimethoxybenzoyl)amino]benzoic acid obtained as above was introduced into the flask and brought into reaction for 20 min while heating the mixture to 120° to 130° C. As soon as the reaction was over, the reaction mixture was poured into 300 ml of 10% aqueous hydrochloric acid solution in a flask under a strong agitation, and the reaction product was extracted two times with each 800 ml of ethyl acetate. The extract was extracted with 500 ml of 1 N aqueous hydroxide solution, and after washing the aqueous extract layer with a small amount of ethyl acetate, the aqueous layer was acidified with aqueous 10% solution of hydrochloric acid and extracted with 800 ml of ethyl acetate. After drying the organic layer, the solvent of the organic layer was evaporated off to obtain a powdery crude product of pale yellowish white in colour. By removing impurities with an addition of 60 ml of acetone to the crude product, 2.0 g of 4-[N-(3',4'-dihydroxybenzoyl)amino]benzoic acid was obtained as a colourless powder in a yield of 36.8%.

The characteristics of the present compound thus obtained were as follows:

(1) melting point on a capillary; 281.0° to 285.0° C. (decomposition);

| (2) elementary analysis; | | | |
|---|---|---|---|
| | C (%) | H (%) | N (%) |
| theoretical: | 61.54 | 4.06 | 5.13 |
| experimental: | 61.30 | 4.30 | 4.85 |

Figure 3:
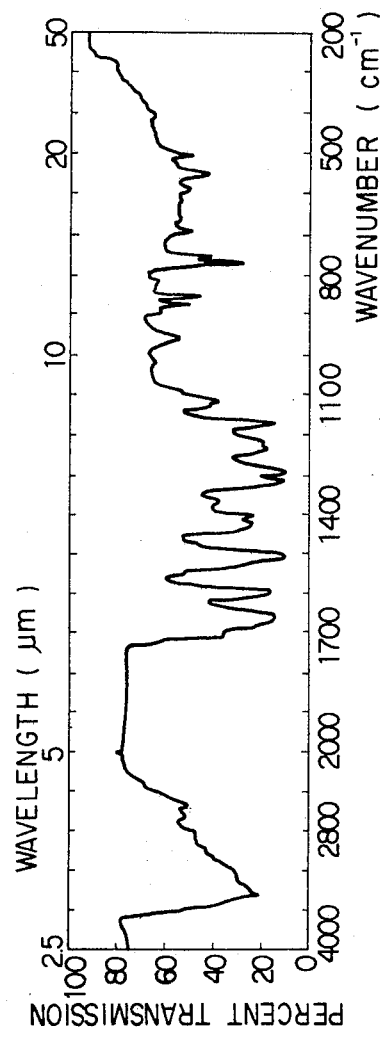

(3) infrared absorption (IR) spectrum by KBr tablet method; shown in FIG. 3.

EXAMPLE 4

Pharmacological activities of the present compound

Inhibitory effect on platelet aggregation:

Rabbit platelet rich plasma (PRP) was used for Aggregation Tests. PRP was prepared by centrifugation of blood collected from the ear vein of Rabbit and diluted into number-concentration 300,000/μl with platelet poor plasma. Platelet aggregation was induced by Sodium Arachidonate and monitored (measured) with a four channel platelet aggregation Tracer PAT-4A (Niko Bioscience Co., Japan). Aggregation Tracer tube containing 230 μl PRP was preincubated at 37° C. for 5 min with each Specimen.

The results are shown in Table 1.

INHIBITORY EFFECT ON POLYNUCLEAR LEUKOCYTE MIGRATION

Inhibitory effect on polynuclear leukocyte migration was examined by using male rats (Donyru) of body weight of about 150 g and Granuloma CMC pouch method (refer to Yakugaku Zasshi, 88, 1472, (1968)).

After shearing the rat on the dorsum about 5 cm in diameter, 5 ml of air was hypodermically injected into the site to form a pouch. After 24 hours, 5 ml of aqueous 2% (w/v) solution of CMC sodium salt at 37° C. was injected into the pouch, and at the same time an aqueous solution of each Specimen was administered perorally to the rat.

After the injection of CMC, the liquid in the pouch was collected as the time passed by in an amount of 0.5 ml and stained. Then the number of polynuclear leukocyte migrated into the pouch was counted.

The results are shown in Table 1.

PROPHYLACTIC EFFECT ON ADJUVANT ARTHRITIS

Prophylactic effect on adjuvant arthritis was examined by using 6 female JCL-SD rats of 8 weeks after birth as one group and conventional method (refer to Fujihira et al., Pharmacometrics, 5(2), 169-183, (1971)).

Freund's complete adjuvant (0.6 mg/0.1 ml) was inoculated into the right hind paw of the etherized rat. After palinesthesia, each specimen was administered perorally once a day for 14 continuous days.

The results are shown in Table 1.

TABLE 1

| | Specimen | |
|---|---|---|
| | Trans-4-[N—(3',4'-dihydroxy-benzoyl)aminomethyl]cyclo-hexane-1-carboxylic acid of the present compound | Sodium trans-4-(N—salicy-loyl-aminomethyl)cyclo-hexane-1-carboxylic acid of the comparative compound |
| Inhibition rate of platelet aggregation (%)[1] | 100 | 10 |
| Inhibition rate of polynuclear leukocyte migration (%)[2] | 35 | 5 |
| Prophylactic effect on adjuvant arthritis (%)[3] | 30 | 5 |

Notes:
[1]The average value of inhibition rate (%) of platelet aggregation at the concentration of 1.5 mM of each Specimen.
[2]The average value of inhibition rate (%) of polynuclear leukocyte migration at the dose of 100 mg p.o./kg body weight of each Specimen determined at 6 hours after the administration.
[3]The average value of prophylactic rate (%) on the adjuvant arthritis at the dose of 100 mg p.o./kg/day for continuous 14 days.

ACUTE TOXICITY

Acute toxicity was examined by administering perorally an aqueous solution of each Specimen to female JCL-ICR mouse of 5 to 6 weeks after birth. As the Specimen, trans-4-[N-(3',4'-dihydroxybenzoyl)aminomethyl]cyclohexane-1-carboxylic acid, 4-[N-(3',4'-dihydroxybenzoyl)amino]benzoic acid and 6-[N-(3',4'-dihydroxybenzoyl)amino]caproic acid were used. Median lethal dose ($LD_{50}$) of each Specimen was more than 3000 mg/kg, and no abnormality on the mouse was found.

As shown above, the present compound has inhibitory effects on platelet aggregation and polynuclear leukocyte migration, and a low toxicity. Accordingly, the present compound is useful as a remedy for various diseases such as inflammation, thrombosis, asthma or cancer, etc., especially for chronic diseases such as rheumatism or systemic lupus erythematosus (SLE), etc.

MANUFACTURE OF THE PHARMACEUTICAL PREPARATIONS

EXAMPLE 5

Manufacture of the capsulated preparation:

Ten parts by weight of trans-4-[N-(3',4'-dihydroxybenzoyl)aminomethyl]cyclohexane-1-carboxylic acid, 15 parts by weight of heavy magnesium oxide and 75 parts by weight of lactose were uniformly mixed to be a pharmaceutical powder, and by putting the thus prepared powder into gelatin capsules, a capsulated preparation was prepared.

EXAMPLE 6

Manufacture of the granular preparation

After mixing uniformly and then kneading 45 parts by weight of trans-4-[N-(3',4'-dihydroxybenzoyl)aminomethyl]cyclohexane-1-carboxylic acid, 10 parts by weight of starch, 20 parts by weight of lactose, 3 parts by weight of polyvinyl alcohol and 22 parts by weight of water, the mixture thus formed was crushed and formulated into granules, and by drying and sifting the dried granules, a granular preparation was obtained.

EXAMPLE 7

Manufacture of the pharmaceutical injection

Into 99.4 parts by weight of aqueous physiological saline solution, 0.6 part by weight of sodium trans-4-[N-(3',4'-dihydroxybenzoyl)aminomethyl]cyclohexane-1-carboxylate was added, and after heating the mixture to be a clear solution, the solution was sterilized to be a pharmaceutical injection.

What is claimed is:

1. A derivative of dihydroxybenzoic acid represented by the formula (I):

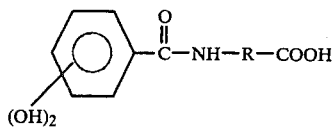

wherein R represents

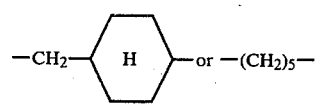

or a salt or an ester thereof.

2. The derivative of claim 1, which is 4-(N-dihydroxybenzoyl aminomethyl)cyclohexane-1-carboxylic acid or a salt or an ester thereof.

3. The derivative of claim 1, which is (N-dihydroxybenzoyl)-ε-aminocaproic acid or a salt or an ester thereof.

4. The derivative of claim 1, which is trans-4-[N-(3',4'-dihydroxybenzoyl)aminomethyl]cyclohexane-1-carboxylic acid or a salt or an ester thereof.

5. A pharmaceutical composition in dosage unit form comprising a therapeutically effective amount of a derivative of dihydroxybenzoic acid represented by the formula (I):

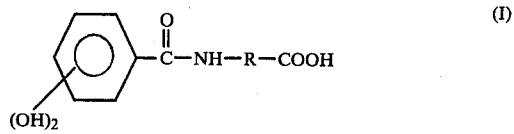

wherein R is as defined in claim 1, or a salt or an ester thereof, and a pharmaceutically acceptable carrier.

* * * * *